(12) United States Patent
Lüddecke et al.

(10) Patent No.: US 6,827,941 B1
(45) Date of Patent: Dec. 7, 2004

(54) USE OF CAROTENOID AGGREGATES AS COLORANTS

(75) Inventors: Erik Lüddecke, Mutterstadt (DE); Helmut Auweter, Limburgerhof (DE); Loni Schweikert, Altrip (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 570 days.

(21) Appl. No.: 09/226,143

(22) Filed: Jan. 7, 1999

(30) Foreign Application Priority Data

Jan. 21, 1998 (DE) .......................... 198 02 134

(51) Int. Cl.$^7$ .................. A61K 7/00; A61K 47/00; A61K 31/12; A61K 31/01
(52) U.S. Cl. .............. 424/401; 424/439; 514/675; 514/762
(58) Field of Search ................ 424/401, 439; 514/675, 762

(56) References Cited

U.S. PATENT DOCUMENTS 5,591,343 A * 1/1997 Kitaoka et al. ............. 210/634

FOREIGN PATENT DOCUMENTS

| JP | 63145367 | * | 6/1988 |
| JP | 08089280 | * | 4/1996 |

OTHER PUBLICATIONS

Photochem . . . vol. 19, pp435–441, Song et al.
J. Photochem. Photobiol. B Biol, 21 (1993) 229–234, Ruban et al.
J. Raman Spectroscopy, vol. 6, No. 6, 1997 Salares et al., 282–288.

* cited by examiner

*Primary Examiner*—Alton N. Pryor
(74) *Attorney, Agent, or Firm*—Keil & Weinkauf

(57) ABSTRACT

Carotenoid aggregates are useful as colorants for foods and for cosmetic and pharmaceutical preparations.

12 Claims, 1 Drawing Sheet

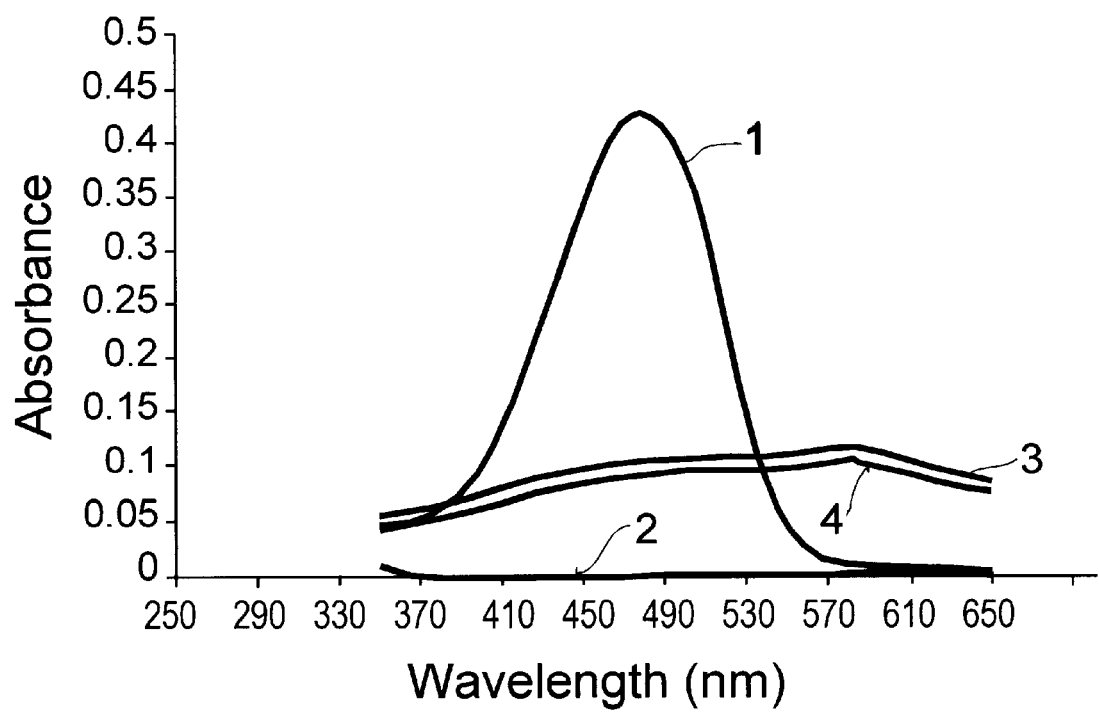

USE OF CAROTENOID AGGREGATES AS COLORANTS

The present invention relates to the use of carotenoid aggregates as colorants.

Carotenoids occur widely in nature and are already being used in various forms for coloring foods, cosmetics and nonfood articles. However, possible uses are greatly limited by the fact that carotenoids are generally very light- and oxygen-sensitive. In practice, therefore, carotenoid-colored preparations have to be protected against light and oxygen, for example by degassing or by storage in opaque vessels.

It is an object of the present invention to provide stable carotenoid colorants without the abovementioned disadvantages.

We have found that this object is achieved according to the present invention by using carotenoid aggregates as colorants.

BRIEF DESCRIPTION OF THE DRAWINGS

FIG. 1 illustrates the UV/VIS spectra of two forms of astaxanthin before and after irradiation.

The aggregation of carotenoids is a well-known phenomenon which has been numerously described in the literature [P. Song, T. A. Moore, Photochemistry and Photobiology, 19, 435–441 (1974); A. V. Ruban, P. Horton, A. J. Young, J. Photochem. Photobiol. B: Biol., 21, 229–234 (1993); V. R. Salares, N. M. Young, P. R. Carey, H. J. Bernstein, Journal of Raman Spectroscopy, 6(6), 282–288 (1977)].

Carotenoid aggregates can be produced, for example, by mixing a solution of a carotenoid in a water-miscible organic solvent such as, for example, isopropanol, ethanol, acetone or tetrahydrofuran with water.

Depending on the choice of mixing ratio between water and organic solvent, either H- or J-aggregates can be produced in this way, as described in the abovementioned literature.

H-aggregates are a card-stack arrangement of the polyene chains which, in the UV/VIS spectrum, is characterized by the appearance of a new band within the range from 320 to 400 nm which represents a hypsochromic shift compared with the absorption of the monomeric forms. J-aggregates, in contrast, represent a linear head-tail arrangement of the polyenes which causes a bathochromic shift in the UV absorption.

These aggregates thus differ in hue from the dissolved monomeric carotenoid and can be identified not only visually by this color shift but also UV/VIS-spectroscopically.

It has now been found that, surprisingly, these carotenoid aggregates exhibit significantly better stability to irradiation with light, for example with a xenon lamp, than the monomeric carotenoids.

Owing to this excellent photostability, the carotenoid aggregates are highly useful for coloring foods, cosmetic preparations and pharmaceutical preparations and also non-food objects, especially those preparations in which the dye is exposed to light.

Of the carotenoid aggregates mentioned at the beginning, the H- and/or J-aggregates are preferred and the J-aggregates are particularly preferred for use as colorants.

The carotenoids useful as colorants in the form of aggregates are the known, natural or synthetic representatives of this class, e.g., β-carotene, lycopene, bixin, zeaxanthin, cryptoxanthin, citranaxanthin, lutein, canthaxanthin, astaxanthin. Particular preference is given to the use of those representatives such as β-carotene, astaxanthin or lycopene, especially astaxanthin and/or lycopene, which are now also readily preparable in industry.

The carotenoid aggregate colorants of the present invention can be used alone or advantageously in the presence of protective colloids.

Examples of protective colloids are gelatin, fish gelatin, starch, dextrin, vegetable proteins, pectin, gum arabic, casein, caseinate or mixtures thereof. However, it is also possible to use polyvinyl alcohol, polyvinylpyrrolidone, methylcellulose, carboxymethylcellulose, hydroxypropylcellulose and alginates. For further details see R. A. Morton, Fat Soluble Vitamins, Intern. Encyclopedia of Food and Nutrition, vol. 9, Pergamon Press 1970, p. 128–131.

To increase the mechanical stability of the carotenoid formulation, it can be advantageous for the colloid to be admixed with a plasticizer, such as sugar or sugar alcohols, e.g., sucrose, glucose, lactose, invert sugar, sorbitol, mannitol or glycerol.

The amounts of protective colloid, plasticizer and carotenoid aggregate are generally chosen to obtain an end product comprising from 0.1 to 100 ppm, preferably from 0.5 to 50 ppm, particularly preferably from 1 to 20 ppm, of carotenoid, preferably astaxanthin or lycopene, from 20 to 200 ppm of a protective colloid, from 20 to 200 ppm of a plasticizer, all ppm data being based on the total mass of the finished preparation, and also, optionally, small amounts of a stabilizer.

To increase the stability of the carotenoids against oxidative degradation, it is advantageous to add stabilizers such as α-tocopherol, t-butylhydroxytoluene, t-butylhydroxyanisole, ascorbic acid or ethoxyquin.

Emulsifiers can be used, for example ascorbyl palmitate, polyglycerol fatty acid esters, sorbitan fatty acid esters, propylene glycol fatty acid esters or lecithin, in a concentration of from 0 to 200% by weight, preferably from 10 to 150% by weight, particularly preferably from 15 to 80% by weight, based on the carotenoid.

In certain circumstances, it can also be advantageous to use, as well as the carotenoid aggregate, a physiologically approved oil such as, for example, sesame oil, corn oil, cottonseed oil, soybean oil or peanut oil and also esters of medium-length chain vegetable fatty acids in a concentration of from 0 to 500% by weight, preferably from 10 to 300% by weight, particularly preferably from 20 to 100% by weight, based on the carotenoid.

The present invention further provides foods comprising carotenoid aggregates, especially aggregates of astaxanthin and/or lycopene, in amounts from 0.1 to 100 ppm, preferably from 0.5 to 50 ppm, particularly preferably from 1 to 20 ppm (based on the total amount of the preparation).

The foods can be, inter alia, dairy products, fats, e.g., margarine, and preferably drinks, for example soft drinks.

The colored drinks can be both transparent and opaque, i.e., cloudy, preparations. The carotenoid aggregates are preferred for coloring transparent drinks preparations. The carotenoid aggregates of the present invention can be incorporated into the drink in the form of an emulsion or a suspension, as a dry powder or as a solubilizate.

When the carotenoid aggregates are used in foods, the organic solvents not approved for foods, for example acetone or THF, can first be gently distilled off without causing the aggregate form to change.

The present invention further provides cosmetic and pharmaceutical preparations comprising from 0.1 to 100 ppm, preferably from 0.5 to 50 ppm, particularly preferably from 1 to 20 ppm, of carotenoid aggregates, based on the total amount of the cosmetic or pharmaceutical preparation.

These cosmetic and pharmaceutical preparations are generally based on a carrier comprising at least one oil phase. However, preparations having an exclusively aqueous basis are also possible in the use of compounds having hydrophilic substituents. Accordingly, oils, oil-in-water and water-in-oil emulsions, creams and pastes, protective lipstick bases or fat-free gels are suitable.

Such cosmetic or pharmaceutical products can accordingly be present in a liquid, pasty or sold form, for example as water-in-oil creams, oil-in-water creams and lotions, aerosol foam creams, gels, oils, grease sticks, powders, sprays or hydroalcoholic lotions.

Examples of customary oil components in cosmetics are liquid paraffin, glyceryl stearate, isopropyl myristate, diisopropyl adipate, cetylstearyl 2-ethylhexanoate, hydrogenated polyisobutene, petrolatum, caprylic acid/capric acid triglycerides, microcrystalline wax, lanolin and stearic acid.

Customary cosmetic ancillaries for use as additives include, for example, coemulsifiers, fats and waxes, stabilizers, thickeners, active biogenic substances, film formers, scents, additional dyes, pearl luster agents, preservatives, pigments, electrolytes (e.g., magnesium sulfate) and pH regulators. Suitable coemulsifiers include preferably known W/O emulsifiers as well as O/W emulsifiers such as polyglycerol esters, sorbitan esters or partially esterified glycerides. Typical examples of fats are glycerides; suitable waxes include beeswax, paraffin wax or microwaxes possibly combined with hydrophilic waxes. Stabilizers which can be employed are metal salts of fatty acids such as magnesium, aluminum and/or zinc stearate. Suitable thickeners include, for example, crosslinked polyacrylic acids and their derivatives, polysaccharides, especially xanthan gum, guar—guar, agar—agar, alginates and Tyloses, carboxymethylcellulose and hydroxyethylcellulose, also fatty alcohols, monoglycerides and fatty acids, polyacrylates, polyvinyl alcohol and polyvinylpyrrolidone. Examples of active biogenic substances are plant extracts, protein hydrolyzates and vitamin complexes. Customary film formers include, for example, hydrocolloids such as chitosan, microcrystalline chitosan or quaternized chitosan, polyvinylpyrrolidone, vinylpyrrolidone/vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearl luster agents include, for example, glycol distearic esters such as ethylene glycol distearate, but also fatty acids and fatty acid monoglycol esters. Dyes which can be used in addition to the carotenoid aggregates are the substances suitable and approved for cosmetic purposes, as tabulated, for example, in the publication "Kosmetische Farbemittel" of the Farbstoffkommission der Deutschen Forschungsgemeinschaft, published in Verlag Chemie, Weinheim, 1984. These dyes are normally employed in a concentration of from 0.001 to 0.1% by weight, based on the total mixture.

The total proportion of the ancillary and additive substances can be within the range from 1 to 80%, preferably within the range from 6 to 40%, by weight, and the non-aqueous proportion (active ingredient) can be within the range from 20 to 80%, preferably within the range from 30 to 70%, by weight, based on the total amount of the preparation. The preparations can be produced in a conventional manner, for example by hot, cold, hot—hot/cold or PIT emulsification.

Preferred cosmetic or pharmaceutical preparations include, for example, transparent formulations in the form of clear emulsions, solubilizates, gels or hydroalcoholic lotions.

The examples hereinbelow illustrate the use of the carotenoid aggregates according to the present invention.

EXAMPLE 1

5 ml of a molecular solution of 50 mg of astaxanthin per liter of acetone were mixed with 95 ml of a mixture of 70 ml of water and 30 ml of acetone at room temperature. J-Aggregates formed within about 30 minutes, as directly indicated by color change from orange to pink. On irradiation of this aggregate solution in an irradiation apparatus (Suntest® from Heraeus) for 10 minutes, no change in color was observed. On irradiation of a comparative solution of molecularly dissolved astaxanthin (2.5 ppm of astaxanthin in acetone) under identical conditions, the color had completely disappeared after 10 minutes.

The UV/VIS spectra measured before and after irradiation illustrate the increased photostability of the J-aggregates of astaxanthin as compared with the monomeric form [see FIG. 1: (1) astaxanthin monomer form prior to irradiation; (2) monomer form after irradiation; (3) astaxanthin J-aggregate prior to irradiation; (4) J-aggregate after irradiation].

EXAMPLE 2

5 ml of a molecular solution of 50 mg of lycopene per liter of isopropanol were mixed with 95 ml of a mixture of 30 ml of water and 70 ml of isopropanol. H-aggregates formed within seconds, as directly indicated by color shift from orange to yellow-orange. On irradiation of this aggregate solution in an irradiation apparatus (Suntest® from Heraeus) for 10 minutes, only a small color change was observed. Irradiation of a comparative solution of molecularly dissolved lycopene (2.5 ppm of lycopene in isopropanol) under identical conditions led to a more pronounced decrease in the color intensity. By diluting and heating the irradiated solutions, it was possible to convert them into the molecularly dissolved state for quantitative analysis. The lycopene present in the solution in aggregate form was 1.5 times stabler than lycopene in monomeric form.

We claim:

1. Drinks comprising carotenoid aggregates.

2. Transparent drinks as claimed in claim 1 comprising astaxanthin and/or lycopene as carotenoids.

3. Drinks as claimed in claim 1 having a carotenoid content of from 0.1 to 100 ppm, based on the total amount of drink.

4. Cosmetic or pharmaceutical preparations comprising carotenoid aggregates.

5. Cosmetic or pharmaceutical preparations as claimed in claim 4 comprising astaxanthin and/or lycopene as carotenoids.

6. Transparent cosmetic or pharmaceutical preparations as claimed in claim 4.

7. Cosmetic, or pharmaceutical preparations as claimed in claim 4 having a carotenoid content of from 0.1 to 100 ppm, based on the total amount of preparation.

8. A method of forming colored compositions of foods, cosmetics or pharmaceuticals comprising adding a carotenoid aggregate to said composition.

9. The method of claim 8 wherein the composition contains 0.1 to 100 ppm of said aggregate, based on the total weight of the composition.

10. The method of claim 8 wherein the aggregates are H- and/or J-aggregates.

11. The method of claim 10 wherein the aggregates are J-aggregates.

12. The method of claim 8 wherein the carotenoid is astaxanthin or lycopene.

* * * * *